United States Patent
Uruma et al.

(10) Patent No.: US 12,202,750 B2
(45) Date of Patent: Jan. 21, 2025

(54) WASTE LIQUID TREATMENT COMPOSITION AND WASTE LIQUID TREATMENT METHOD

(71) Applicant: DAIKEN MEDICAL CO., LTD., Osaka (JP)

(72) Inventors: Masayuki Uruma, Osaka (JP); Satoru Toyoshima, Osaka (JP)

(73) Assignee: DAIKEN MEDICAL CO., LTD., Osaka (JP)

( * ) Notice: Subject to any disclaimer, the term of this patent is extended or adjusted under 35 U.S.C. 154(b) by 819 days.

(21) Appl. No.: 17/423,000

(22) PCT Filed: Jan. 17, 2020

(86) PCT No.: PCT/JP2020/001456
§ 371 (c)(1),
(2) Date: Jul. 14, 2021

(87) PCT Pub. No.: WO2020/153247
PCT Pub. Date: Jul. 30, 2020

(65) Prior Publication Data
US 2022/0098064 A1    Mar. 31, 2022

(30) Foreign Application Priority Data
Jan. 25, 2019    (JP) ................. 2019-011239

(51) Int. Cl.
*C02F 1/52* (2023.01)
*C02F 1/00* (2023.01)
(Continued)

(52) U.S. Cl.
CPC ............ *C02F 1/5236* (2013.01); *C02F 1/001* (2013.01); *C02F 1/283* (2013.01); *C02F 1/56* (2013.01);
(Continued)

(58) Field of Classification Search
None
See application file for complete search history.

(56) References Cited

U.S. PATENT DOCUMENTS

| 5,350,551 A | 9/1994 | Shino |
| 5,614,102 A | 3/1997 | Sakurada |
| (Continued) | | |

FOREIGN PATENT DOCUMENTS

| CN | 103466732 | 12/2013 |
| CN | 104229957 | 12/2014 |
| (Continued) | | |

OTHER PUBLICATIONS

Partial Supplementary European Search Report issued Jan. 31, 2022 in corresponding European Patent Application No. 20744726.9.
(Continued)

*Primary Examiner* — Richard C Gurtowski
(74) *Attorney, Agent, or Firm* — Wenderoth, Lind & Ponack, L.L.P.

(57) ABSTRACT

One aspect of the present invention relates to a waste liquid treatment composition for treating a waste liquid containing a body fluid to separate the waste liquid into a supernatant and an aggregate in a container. The waste liquid treatment composition comprises: a solid flocculant having at least one group selected from the group consisting of an OH group, an NH group, and an FH group; and a solid compound having at least one group selected from the group consisting of an OH group, an NH group, and an FH group.

12 Claims, 20 Drawing Sheets

(51) Int. Cl.
*C02F 1/28* (2023.01)
*C02F 1/56* (2023.01)
*C02F 103/00* (2006.01)

(52) U.S. Cl.
CPC .... *C02F 2103/003* (2013.01); *C02F 2305/14* (2013.01)

(56) References Cited

U.S. PATENT DOCUMENTS

| | | | | |
|---|---|---|---|---|
| 5,945,004 | A | 8/1999 | Ohira et al. | |
| 2002/0179514 | A1* | 12/2002 | Anderson | D06F 39/20 |
| | | | | 210/258 |
| 2008/0213819 | A1* | 9/2008 | Besson-Faure | B01L 3/5021 |
| | | | | 435/283.1 |
| 2010/0331484 | A1* | 12/2010 | Swift | C08L 61/32 |
| | | | | 524/597 |
| 2018/0008757 | A1* | 1/2018 | Bannwart | A61M 1/60 |

FOREIGN PATENT DOCUMENTS

| | | |
|---|---|---|
| CN | 105936566 | 9/2016 |
| CN | 106186239 | 12/2016 |
| CN | 106830139 | 6/2017 |
| CN | 107724082 | 2/2018 |
| CN | 107892374 | 4/2018 |
| JP | 2-157083 | 6/1990 |
| JP | 7-60231 | 3/1995 |
| JP | 11-299844 | 11/1999 |
| JP | 2000-70611 | 3/2000 |
| JP | 2003-201373 | 7/2003 |
| JP | 2006-122795 | 5/2006 |
| JP | 2007-271388 | 10/2007 |
| JP | 2012-11363 | 1/2012 |
| JP | 2018-202277 | 12/2018 |
| JP | 2018-202283 | 12/2018 |
| WO | 91/11392 | 8/1991 |
| WO | 97/27883 | 8/1997 |

OTHER PUBLICATIONS

Office Action issued Jun. 29, 2022 in corresponding Chinese Patent Application No. 202080009632.8, with Abstract.
Japanese Office Action issued Apr. 4, 2023 in corresponding Japanese Patent Application No. 2019-011239, with English machine translation.
International Search Report issued Feb. 10, 2020 in International (PCT) Application No. PCT/JP2020/001456.

* cited by examiner

WASTE LIQUID TREATMENT COMPOSITION AND WASTE LIQUID TREATMENT METHOD

TECHNICAL FIELD

The present invention relates to a waste liquid treatment composition for treating a waste liquid containing a body fluid, and a method for treating a waste liquid using such a waste liquid treatment composition.

BACKGROUND ART

A waste liquid containing a body fluid, discharged from a patient during surgery or medical treatment, or a waste liquid containing a body fluid, collected from a healthy person and discharged after being used for examination, or the like is discarded after being subjected to an appropriate treatment. These waste liquids include, for example, blood and a body cavity irrigation liquid and the like, but the waste liquids may cause nosocomial infection regardless of the routes of acquisition of the waste liquids. Therefore, it is necessary to pay close attention to the treatment of such waste liquids in terms of safety. Several techniques have been proposed so far for methods for treating the waste liquids as described above.

For example, in a waste liquid treatment method disclosed in Patent Literature 1, a waste liquid containing a body fluid, discharged from a patient during surgery or medical treatment is housed in a container, and a flocculant is charged into the waste liquid in the container, followed by stirring, to separate the waste liquid into a supernatant and an aggregate. Then, the supernatant is discharged from the container, and the aggregate remaining in the container is incinerated together with the container, and discarded. When the supernatant is discharged from the container, the supernatant from the container is caused to pass through a filter to filter and separate the aggregate mixed in the supernatant.

In this waste liquid treatment method, the supernatant discharged from the container is subjected to a treatment such as heat sterilization, and the remaining aggregate including the aggregate which is mixed in the supernatant and separated by the filter is incinerated together with the container, whereby a waste liquid treatment can be safely performed. Since the supernatant is discharged from the container, the volume of a waste in the container can be reduced, which is also advantageous in terms of handleability.

However, the concentrations of blood contained in the waste liquids are different for containers housing the waste liquids, and thus it is necessary to adjust the length of a stirring time depending on the concentration. Therefore, a waste liquid treatment composition capable of efficiently treating a waste liquid without strictly setting a stirring time, and a useful method for treating the waste liquid using such a waste liquid treatment composition are required.

CITATION LIST

Patent Literature

Patent Literature 1: WO 97/27883

SUMMARY OF INVENTION

One aspect of the present invention is a waste liquid treatment composition for treating a waste liquid containing a body fluid to separate the waste liquid into a supernatant and an aggregate in a container, the waste liquid treatment composition comprising: a solid flocculant having at least one group selected from the group consisting of an OH group, an NH group, and an FH group; and a solid compound having at least one group selected from the group consisting of an OH group, an NH group, and an FH group.

A waste liquid treatment method according to another aspect of the present invention comprises: a separation step of housing a waste liquid containing a body fluid in a container, and charging the waste liquid treatment composition according to the present embodiment into the waste liquid in the container, followed by stirring to separate the waste liquid into a supernatant and an aggregate; and a step of discarding the supernatant through a filter.

DESCRIPTION OF EMBODIMENTS

Figure 1:
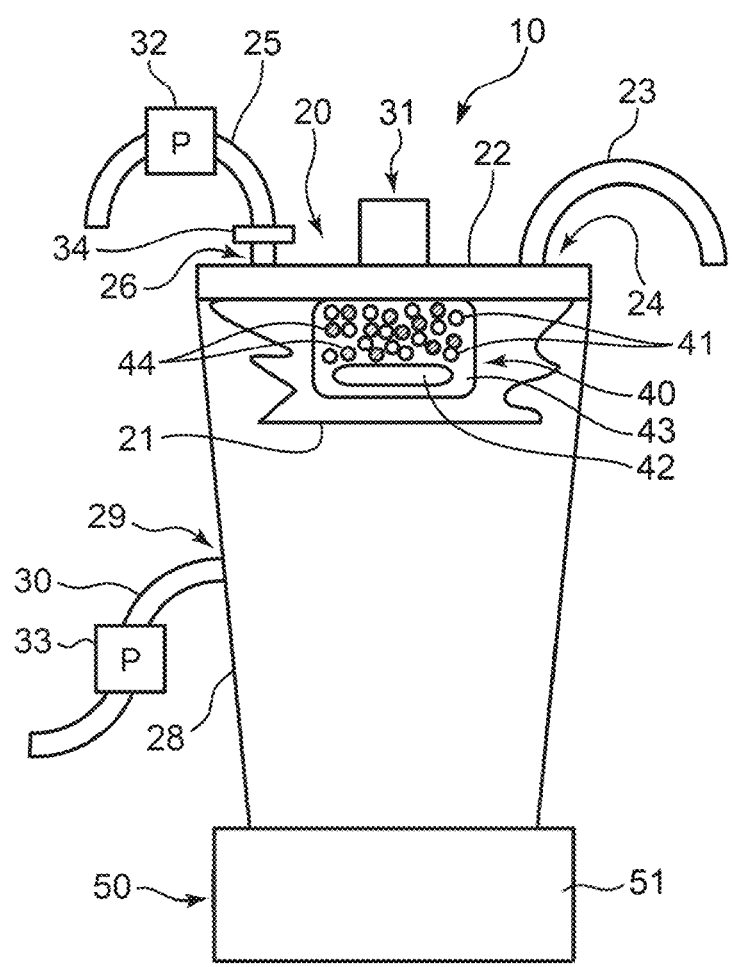
FIG. 1 is a front view schematically showing a configuration example of a waste liquid treatment device when a waste liquid treatment method of the present embodiment is performed.

Usually, the concentrations of blood contained in waste liquids are different for containers in which the waste liquids are housed. It is ideal that when the waste liquid is treated by the method as described above, a stirring time for separating the waste liquid into a supernatant and an aggregate is more strictly set according to the concentration of blood in the waste liquid.

However, it is difficult to strictly set the stirring times according to the concentrations of blood in the waste liquids with respect to the waste liquids having different concentrations of blood for the containers. On the other hand, when appropriate stirring times are not set according to the concentrations of blood in the waste liquids, it causes various disadvantages. For example, when a stirring time is set to be short on the assumption of a waste liquid in which is the low concentration of blood (hereinafter, may be referred to as "low concentration blood waste liquid"), the stirring time becomes insufficient in a waste liquid in which an actual concentration of blood is higher than an assumed concentration (hereinafter, may be referred to as "high concentration blood waste liquid"), so that an aggregate in which blood is not sufficiently coagulated is formed.

The waste liquid treatment as described above is preferably performed under full automation. However, in performing such full automation, a step of measuring the concentration of blood in the waste liquid is required in order to set an appropriate stirring time according to the concentration of blood in the waste liquid. That is, the necessity of the step of measuring the concentration of blood in the waste liquid also becomes an obstacle in performing full automation.

The aggregate in which blood is not sufficiently coagulated becomes an aggregate which is fine and has low strength of aggregation. When the stirring time is not sufficient, blood cells remaining without being sufficiently coagulated are mixed in the supernatant. Such blood cells are also likely to form an aggregate which is fine and has low strength of aggregation in the supernatant. An increase in the aggregate which is fine and has low strength of aggregation may cause clogging of a filter to occur.

Conversely, in the case where the stirring time is set to be long on the assumption that the waste liquid is the high concentration blood waste liquid, and the waste liquid is actually the low concentration blood waste liquid, even when an aggregate which is large and has high strength of aggregation is initially formed, the aggregate is disintegrated by stirring for a long time. Blood returns to a state of not being sufficiently coagulated, and is mixed into the supernatant, which may cause the clogging of the filter to occur as described above.

For this reason, in order to reduce the occurrence of the clogging of the filter when the waste liquid is separated into the supernatant and the aggregate, the aggregate to be separated is desirably an aggregate which is relatively large and has high strength of aggregation. The fact that the aggregate to be formed is relatively large and has high strength of aggregation is also a necessary requirement from the viewpoint of handleability after the waste liquid treatment.

The present invention has been made under the above-described circumstances, and an object of the present invention is to provide a waste liquid treatment composition capable of efficiently treating the waste liquid without strictly setting the stirring time, to obtain the aggregate which is relatively large and has high strength of aggregation, and of reducing the occurrence of the clogging of the filter, and a useful method for treating the waste liquid using such a waste liquid treatment composition.

The present inventors have conducted studies from various angles in order to achieve a waste liquid treatment composition capable of efficiently treating a waste liquid containing a body fluid to obtain an aggregate which is relatively large and has high strength. As a result, the present inventors have found that when a waste liquid is treated using a waste liquid treatment composition comprising a solid flocculant having at least one group selected from the group consisting of an OH group, an NH group, and an FH group and a solid compound having at least one group selected from the group consisting of an OH group, an NH group, and an FH group, the waste liquid can be effectively separated into a supernatant and an aggregate without strictly setting the stirring time, and the separated aggregate can be relatively large and have high strength, which makes it possible to prevent a disadvantage of the occurrence of the clogging of the filter, and have completed the present invention.

That is, a waste liquid treatment composition of the present embodiment is a waste liquid treatment composition for treating a waste liquid containing a body fluid to separate the waste liquid into a supernatant and an aggregate in a container, the waste liquid treatment composition comprising: a solid flocculant having at least one group selected from the group consisting of an OH group, an NH group, and an FH group; and a solid compound having at least one group selected from the group consisting of an OH group, an NH group, and an FH group.

The above configuration makes it possible to provide the waste liquid treatment composition capable of efficiently treating the waste liquid without strictly setting the stirring time to obtain the aggregate which is relatively large and has high strength of aggregation and of reducing the occurrence of the clogging of the filter, and a useful method for treating the waste liquid using the waste liquid treatment composition.

Hereinafter, embodiments according to the present invention will be specifically described, but the present invention is not limited thereto.

(Flocculant)

The flocculant used in the waste liquid treatment composition of the present embodiment flocculates components such as blood contained in the waste liquid to form the aggregate in the container. The flocculant, for example, flocculates red blood cells which are cell components contained in blood.

As the flocculant used in the present embodiment, a solid flocculant such as a powdery, granular, or lump flocculant is used. However, in order to facilitate the dispersion of the flocculant in a liquid layer in a waste liquid treatment to be described later, the flocculant is preferably in a powdery form or a granular form.

The solid flocculant used in the present embodiment has at least one group selected from the group consisting of an OH group, an NH group, and an FH group. An aggregate which is relatively large and has high strength of aggregation is formed by the interaction between the flocculant and the solid compound used in the present embodiment, that is, the solid compound having at least one group selected from the group consisting of an OH group, an NH group, and an FH group.

The flocculant used in the present embodiment preferably has a positive charge from the viewpoint of being likely to take components such as blood having a negatively charged surface in the aggregate. Such a flocculant may be an inorganic flocculant such as polyaluminum chloride, aluminum sulfate (an aggregation of aluminum sulfate), or polyferric chloride. Even these inorganic flocculants form a hydroxy group (—OH group) in water. However, in consideration of obtaining an aggregate which is large and has higher strength of aggregation, a polymer flocculant which is an organic flocculant is preferable.

The polymer flocculant preferably has at least a positive charge (cation) from the viewpoint of being likely to take components such as blood having a negatively charged surface in the aggregate, and preferable examples of the polymer flocculant include cationic polymer flocculants such as a polyacrylic acid ester, a polymethacrylic acid ester, and polyvinyl amidine, as well as an amphoteric polymer flocculant.

However, the cationic polymer flocculant used in the present embodiment is not limited to the above-described flocculants, and may be a homopolymer of dimethylaminoethyl(meth)acrylate having a cation, or a copolymer of dimethylaminoethyl(meth)acrylate and acrylamide, or the like. Preferable examples of the amphoteric polymer flocculant include a copolymer of dimethylaminoethyl(meth)acrylate, acrylamide, and acrylic acid.

In the above description, the flocculant having an OH group has been mainly described, but a flocculant having an NH group or an FH group can be used. Examples of the flocculant having an NH group include acrylamide (nonionic polymer flocculant), a cationic monomer acrylamide copolymer (cationic polymer flocculant), and a sodium acrylamidoacrylate copolymer (anionic polymer flocculant).

(Solid Compound)

The waste liquid treatment composition of the present embodiment also contains a solid compound having at least one group selected from the group consisting of an OH group, an NH group, and an FH group. The waste liquid treatment composition comprises the solid flocculant and the solid compound, whereby when the waste liquid is treated using the waste liquid treatment composition of the present embodiment, the formed aggregate is relatively large, and has high strength of aggregation. Furthermore, the blood cells remaining without being coagulated are less likely to be mixed in the supernatant. In addition, the aggregate once formed is suppressed from being disintegrated even by stirring for a long time. When the waste liquid is treated using the waste liquid treatment composition of the present embodiment, the occurrence of the clogging of the filter caused by the aggregate is reduced.

Preferable examples of the solid compound used in the present embodiment include a boron-containing compound. The boron-containing compound may be any compound as long as the compound forms a hydrogenborate ion having a hydroxy group (—OH group) when the compound is charged into the waste liquid, and preferable examples thereof include boric acid, ulexite, borax, and kernite. These compounds may be used singly or in combination of two or more thereof. Among these, the most preferable compound is borax from the viewpoint of being dissolved regardless of the temperature of the waste liquid.

In the above description, the compound having an OH group has been mainly described, but a compound having an NH group or an FH group can be used. Examples of the compound having an NH group when being charged into the waste liquid include nitrogen compounds such as titanium nitride (TiN), zirconium nitride (ZrN), and aluminum nitride (AlN). Examples of the compound having an FH group when being charged into the waste liquid include calcium fluoride (CaF), aluminum fluoride (AlF), sodium fluoride (NaF), and potassium fluoride (KF).

(Waste Liquid Treatment Method)

By using the waste liquid treatment composition of the present embodiment, a waste liquid containing a body fluid can be effectively separated into a supernatant and an aggregate, and discarded. That is, a waste liquid treatment method of the present embodiment is a waste liquid treatment method comprising: a separation step of housing a waste liquid containing a body fluid in a container, charging the waste liquid treatment composition of the present embodiment into the waste liquid in the container, followed by stirring to separate the waste liquid into a supernatant and an aggregate; and a step of discarding the supernatant through a filter.

In the waste liquid treatment method of the present embodiment, the amount of the flocculant charged into the waste liquid is preferably 0.02% by mass or more with respect to the entire waste liquid. More preferably, the amount of the flocculant charged into the waste liquid is 0.05% by mass or more. By setting the amount of the flocculant charged into the waste liquid to 0.02% by mass or more with respect to the entire waste liquid, the effect is effectively exhibited. The upper limit of the amount of the flocculant charged into the waste liquid is not limited at all, but the upper limit of the amount is preferably 0.3% by mass or less, and more preferably 0.15% by mass or less from the viewpoint of the saturation of the effect.

The amount of the solid compound charged into the waste liquid is preferably 0.02% by mass or more with respect to the entire waste liquid. More preferably, the amount of the solid compound charged into the waste liquid is 0.03% by mass or more. By setting the amount of the solid compound charged into the waste liquid to 0.02% by mass or more with respect to the entire waste liquid, the effect is effectively exhibited. The upper limit of the amount of the solid compound charged into the waste liquid is not limited at all, but the upper limit of the amount is preferably 0.8% by mass or less, and more preferably 0.11% by mass or less from the viewpoint of the saturation of the effect.

In the waste liquid treatment composition, the content ratios of the solid flocculant and solid compound may be adjusted such that the amount of each component charged falls within the above range.

A slime is formed while moisture is taken in together with components such as blood into gaps of the formed aggregate. Therefore, blood and the like in the waste liquid remaining without being coagulated can be taken into the slime while being reduced as much as possible, and as a result, an aggregate which is relatively large and has high strength of aggregation is formed.

Meanwhile, when an inorganic flocculant is used, the strength of aggregation of an aggregate to be formed is slightly reduced. However, by containing the solid compound, a certain degree of strength of aggregation can be secured as compared with the case where the waste liquid is treated with the inorganic flocculant alone. That is, when the waste liquid is treated with the inorganic flocculant alone, the waste liquid becomes a relatively small aggregate in which components such as blood cells are coagulated with each other, and such an aggregate is apt to be disintegrated by stirring for a long time. However, it is presumed that the relatively small aggregates can be firmly bonded to each other due to the simultaneous presence of the solid compound, and the aggregates are less likely to be disintegrated even by stirring for a long time.

The waste liquid containing a body fluid may contain not only components such as blood and physiological saline but also oil-and-fat components such as fat. In order to remove such oil-and-fat components, the waste liquid treatment composition of the present embodiment may contain an oleosity adsorbing agent as necessary. Preferable examples of such an oleosity adsorbing agent include activated carbon. When the oleosity adsorbing agent is contained, the content of the oleosity adsorbing agent in the waste liquid treatment composition is preferably adjusted such that the amount of the oleosity adsorbing agent charged into the waste liquid is 0.02 to 0.3% by mass with respect to the entire waste liquid. The amount charged is more preferably 0.05% by mass or more and 0.15% by mass or less. When the oleosity adsorbing agent is contained in the waste liquid treatment composition together with the solid flocculant and the solid compound described above, the solid flocculant, the solid compound, and the oleosity adsorbing agent may be blended at a ratio of 1:1:1 without strictly adjusting the content ratios (mass ratios) thereof in the waste liquid treatment composition.

In the container in which the waste liquid containing the body fluid is housed, in addition to the above-described oil-and-fat components, floating substances such as blood clots and bubbles derived from the body fluid may float in the waste liquid. When the floating substances float, and a solid flocculant such as a powdery or granular flocculant is used as the flocculant, the solid flocculant adheres to the floating substances before being brought into contact with the waste liquid even if the flocculant is directly charged into the container in which the waste liquid is housed, so that the flocculant may not sufficiently spread in the waste liquid. As a result, the efficiency of separating the waste liquid into the supernatant and the aggregate is reduced. It is preferable that the solid compound used in the present embodiment is also basically in a powdery form or a granular form.

When the waste liquid is treated using the waste liquid treatment composition of the present embodiment, it is preferable to use a waste liquid treatment method capable of solving the problems as described above. That is, more preferable examples of the waste liquid treatment method of the present embodiment include a waste liquid treatment method further including a contact step of bringing a waste liquid treatment composition unit containing a waste liquid treatment composition and a water-soluble member into contact with a waste liquid in the container, to dissolve a part or a whole of the water-soluble member in the waste liquid, and thus causing the waste liquid to contain the waste liquid treatment composition.

The waste liquid treatment method of the preferable embodiment makes it possible to prevent the solid flocculant such as a powdery or granular flocculant and the boron-containing compound from being brought into direct contact with the floating substances floating in the waste liquid in the container. As a result, the waste liquid treatment composition can be brought into contact with the waste liquid from the dissolved portion. This causes no problem that the waste liquid treatment composition does not sufficiently spread in the waste liquid due to the adhesion of the waste liquid treatment composition to the floating substances before contact with the waste liquid. Accordingly, the waste liquid treatment method of this embodiment can cause the waste liquid to sufficiently contain the waste liquid treatment composition in the contact step, whereby a desired amount of the waste liquid treatment composition can be dispersed in the waste liquid by stirring the waste liquid in the separation step.

As a result, the waste liquid treatment composition causes the components contained in the waste liquid to efficiently become the aggregate, whereby the waste liquid can be efficiently separated into the supernatant and the aggregate in the container. The separated supernatant is discharged from the container and subjected to an appropriate treatment, for example, to be safely discarded. The separated aggregate is subjected to an appropriate treatment such as an incineration treatment together with the container or separately from the container, to be safely discarded. By applying such a waste liquid treatment method, the waste liquid having the floating substances can be efficiently treated even when the solid flocculant such as a powdery or granular flocculant and the boron-containing compound are used.

Hereinafter, a waste liquid treatment method of a preferable embodiment will be specifically described with reference to the drawings showing a configuration example of a waste liquid treatment device. However, the waste liquid treatment device for performing the waste liquid treatment method of the present embodiment is not limited to the illustrated configuration. In the drawings in the description to be described later, main reference numerals are as follows: 20, container; 21, container body; 22, upper lid; 28, holding container; 31, dropping mechanism; 40, waste liquid treatment composition unit; 41, solid flocculant; 42, stirrer; 43, water-soluble member; 44, solid compound (boron-containing compound); 50, stirring device; 70, waste liquid; and 72, floating substances.

FIG. 1 is a front view schematically showing an example of a waste liquid treatment device 10 used when the waste liquid treatment method of the present embodiment is performed. The waste liquid treatment device 10 includes a container 20, a holding container 28, a waste liquid treatment composition unit 40, and a stirring device 50. The container 20 includes a container body 21 and an upper lid 22. The container body 21 holds a waste liquid sucked and flowing into the container 20. The container body 21 has deformable flexibility.

Accordingly, the container body 21 is configured such that the internal volume of the container body 21 increases or decreases according to a difference between the pressures inside and outside the container 20. The pressure outside the container is a pressure of a space between the holding container 28 and the container body 21 to be described later. The container body 21 is formed of a material which can be easily deformed, such as a soft synthetic resin.

The container 20 is configured to be separable from the holding container 28. At a preparation stage of treating the waste liquid, the container 20 is attached to the holding container 28 in a state where the container body 21 is contracted, to be brought into the state shown in FIG. 1. Accordingly, the container body 21 is housed in the holding container 28, and an upper opening part of the holding container 28 is closed by the upper lid 22.

One end of a tube 23 is connected to a connection port 24 provided in the upper lid 22, and one end of a tube 25 is connected to a connection port 26. One end of a tube 30 is connected to a connection port 29 provided in the holding container 28.

As shown in FIG. 1, before the container body 21 is used for a waste liquid treatment, for example, the container body 21 forms a plurality of fold lines in a zigzag form, and is in a contracted state such that the internal volume of the container 20 is reduced.

Figure 2:
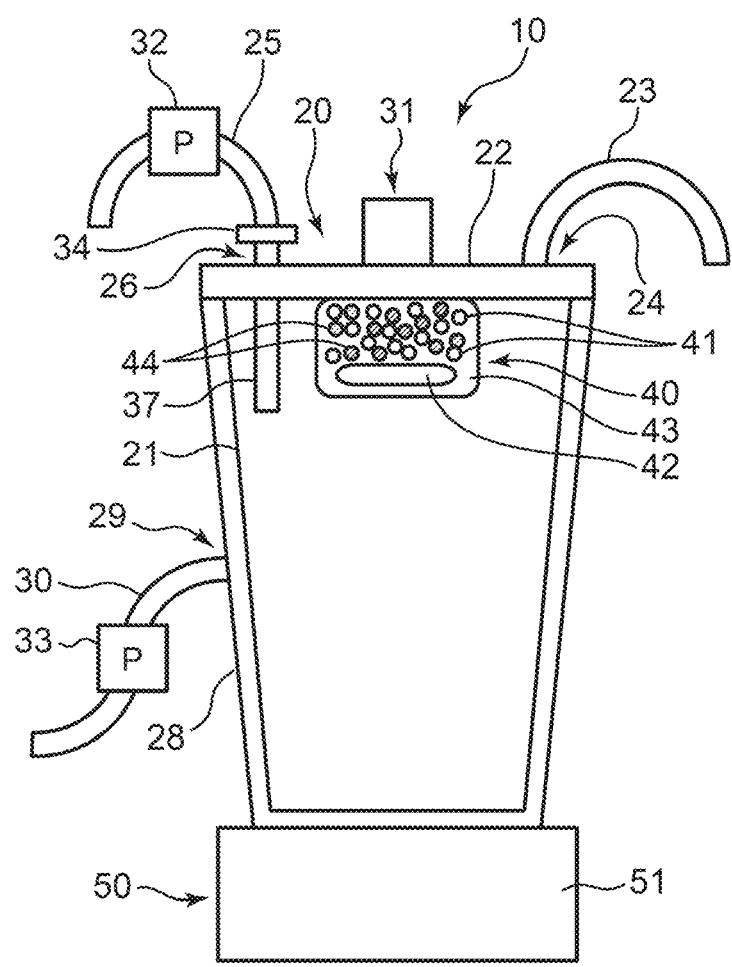
FIG. 2 is a front view schematically showing a preparation step in the waste liquid treatment method of the present embodiment.

When the container 20 is used for a waste liquid treatment, the pressures inside and outside the container 20 are adjusted such that the pressure inside the container 20 is greater than the pressure outside the container 20. Accordingly, as shown in FIG. 2, the fold lines of the container body 21 expansively extend such that the internal volume of the container 20 increases. In the present embodiment, the container body 21 is configured to be stretchable (deformable) as described above, but the present invention is not limited thereto. The container body 21 may be configured so as not to be deformed in the same shape before and after use.

The container 20 is configured as a disposable container. That is, the container 20 is discarded together with the waste liquid treatment composition housed in the container 20 in a discard step to be described later. However, the container 20 may be not necessarily a disposable container, and may be configured to be reusable by performing an appropriate treatment such as sterilization or cleaning after performing the waste liquid treatment method of the present embodiment.

The upper lid 22 closes an upper opening part of the container body 21. As shown in FIGS. 1 and 2, the upper lid 22 includes the connection port 24 and the connection port 26. The tube 23 for guiding the waste liquid into the container 20 in a contact step is connected to the connection port 24. The tube 25, which discharges air in the container 20 to the outside of the container body 21 in the contact step, is connected to the connection port 26.

As shown in FIG. 1, the waste liquid treatment composition unit 40 is supported by the container 20 at a predetermined position in the container 20. Specifically, the waste liquid treatment composition unit 40 is attached to the upper lid 22 of the container 20, and supported by the upper lid 22.

In the present embodiment, the waste liquid treatment composition unit 40 is supported by the container 20 before use as described above (specifically, the waste liquid treatment composition unit 40 is supported by the lower surface of the upper lid 22). Meanwhile, the waste liquid treatment composition unit 40 is removed from the container 20 (specifically, the lower surface of the upper lid 22), and dropped into the waste liquid at an appropriate time point of the contact step to be described later.

In the present embodiment, the upper lid 22 includes a dropping mechanism 31. The dropping mechanism 31 drops the waste liquid treatment composition unit 40 into the waste liquid housed in the container 20 in the contact step. The dropping mechanism 31 is configured to release the support of the waste liquid treatment composition unit 40 by the container 20 (specifically, the support of the waste liquid treatment composition unit by the upper lid 22) by an operation from the outside of the container 20 so that the waste liquid treatment composition unit 40 can be dropped into the waste liquid in the container 20. The operation may be manually performed by an operator, or may be automatically performed by a control part of the waste liquid treatment device 10.

Specifically, the dropping mechanism 31 is, for example, a dropping button which can be operated from the outside of the container 20 by an operator performing a waste liquid treatment. The operator pushes down the dropping button, so that the waste liquid treatment composition unit 40 supported by the upper lid 22 is pushed downward to be detached from the upper lid 22, and falls toward the liquid level of the waste liquid. The dropping mechanism 31 is not limited to the dropping button shown in FIG. 1, and any other mechanism can be adopted as long as the waste liquid treatment composition unit 40 can be dropped into the waste liquid by the operator manually or the control part of the waste liquid treatment device 10 automatically at an appropriate time point in the contact step.

As shown in FIGS. 1 and 2, the container 20 is held by the holding container 28. The holding container 28 has rigidity enough to hold the container 20. The holding container 28 is a container capable of housing the entire container body 21. As shown in FIG. 1, the upper opening part of the holding container 28 is closed by the upper lid 22 of the container 20.

As shown in FIGS. 1 and 2, the holding container 28 includes the connection port 29. The tube 30 is connected to the connection port 29. The tube 30 sucks air in the space between the holding container 28 and the container body 21 in a preparation step and a connection step and the like to be described later to make the pressure of the space smaller than the pressure inside the container body 21, thereby bringing the container body 21 from a contracted state to an extended state or maintaining the extended state.

The holding container 28 is configured as a reusable container. That is, the holding container 28 is subjected to an appropriate treatment such as sterilization or cleaning after being used in the waste liquid treatment method according to the present embodiment, and reused.

As shown in FIGS. 1 and 2, the waste liquid treatment composition unit 40 includes a flocculant 41, a stirrer 42, a solid compound 44, and a water-soluble member 43 housing the flocculant 41, the stirrer 42, and the solid compound 44. Hereinafter, the solid compound 44 may be referred to as a boron-containing compound 44.

The amounts of the flocculant 41 and the boron-containing compound 44 contained in the waste liquid treatment composition unit 40 are adjusted to the preferable charged amount described above, for example, in consideration of the volume of the container body 21, and the like. The particle sizes of the powdery or granular flocculant 41 and the boron-containing compound 44 are not particularly limited, and are appropriately set in consideration of ease of dispersion of the waste liquid in the liquid layer in the contact step to be described later, and the like.

The stirrer 42 is used to stir the liquid layer in the container 20 in a stirring step to be described later. Since the stirring device 50 to be described later is a magnetic stirrer, as the stirrer 42, for example, an elongated stirrer in which a bar magnet is covered with a synthetic resin or the like can be used. The stirrer 42 is an example of a weight adjusting member, and also has a function of adjusting the weight of the waste liquid treatment composition unit 40. The mass of the stirrer 42 is adjusted such that a part or a whole of the waste liquid treatment composition unit 40 dropped into the waste liquid in the contact step to be described later passes through the floating substances and reaches the waste liquid below the floating substances. Specifically, as the stirrer 42, a stirrer having a specific gravity greater than that of blood contained in the waste liquid can be used. The mass of the stirrer 42 is preferably adjusted such that the entire mass of the waste liquid treatment composition unit 40 is greater than the mass of the waste liquid having the same volume as that of the waste liquid treatment composition unit 40.

As a material constituting the water-soluble member 43, for example, a water-soluble synthetic resin or the like can be used. Examples of such a synthetic resin include, but are not limited to, polyvinyl alcohol. For example, water-soluble paper may be used. By using such water-soluble paper as a material of the water-soluble member, the dissolution of the water-soluble member rapidly proceeds when the waste liquid treatment composition unit is brought into contact with the waste liquid, which accordingly provides increased waste liquid treatment efficiency. A time from the contact of the water-soluble member with the waste liquid to the contact of the internal waste liquid treatment composition with the waste liquid by the dissolution of the water-soluble member can be appropriately adjusted by changing the material constituting the water-soluble member, and the thickness of the water-soluble member, and the like.

The powdery or granular flocculant 41, the stirrer 42, and the boron-containing compound 44 are housed in the water-soluble member 43. Specifically, for example, one sheet of water-soluble paper is folded in two to be stacked, or two sheets of water-soluble paper are stacked, and peripheral portions of the sheets of water-soluble paper are bonded using a bonding method such as fusion in a state where the flocculant 41, the stirrer 42, and the boron-containing compound are disposed between the sheets of water-soluble paper. Accordingly, the waste liquid treatment composition unit 40 in which the flocculant 41 and the stirrer 42 are sealed is obtained.

The flocculant 41, the stirrer 42, and the boron-containing compound 44 are not necessarily sealed with a water-soluble film, and the housing space may slightly communicate with the outside of the waste liquid treatment composition unit 40. That is, before the water-soluble film is brought into contact with the liquid layer in the contact step, the flocculant 41, the stirrer 42, and the boron-containing compound 44 may be surrounded and held by the water-soluble film to the extent that the flocculant 41, the stirrer 42, and the boron-containing compound 44 do not come out of the housing space of the water-soluble film.

The stirring device 50 stirs the waste liquid in the container 20 in a stirring step to be described later. In the present embodiment, a magnetic stirrer is used as the stirring device 50. The stirring device 50 (magnetic stirrer 50) includes a main body 51 and the stirrer 42 described above. That is, in the present embodiment, the stirrer 42 constitutes a part of the waste liquid treatment composition unit 40, and also constitutes a part of the stirring device 50.

The main body 51 of the magnetic stirrer 50 includes a drive part and a control part which are not shown, and a housing which houses the drive part and the control part, and the like. The rotational speed of the stirrer 42 is adjusted by the drive part or the control part. The holding container 28 is set on a top plate of the housing of the magnetic stirrer 50. As the stirring device 50, for example, another stirring device such as a mechanical stirrer which causes the rotation of a rotation shaft connected to a motor to stir the waste liquid can also be used.

Next, an example of the waste liquid treatment method according to the present embodiment will be described. The waste liquid treatment method according to the present embodiment can include, for example, a preparation step, a contact step, a separation step, a discharge step, and a discard step as described below.

(Preparation Step)

First, the preparation step will be described. The preparation step is performed before the contact step to be described later, and makes it possible to suck the waste liquid into the container 20 in the contact step.

In the preparation step, as shown in FIG. 1, the holding container 28 is set on the main body 51 of the stirring device 50. As shown in FIG. 1, the container 20 is attached to the holding container 28 in a state where the container body 21 is contracted as shown in FIG. 1. Accordingly, the container body 21 is housed in the holding container 28, and an upper opening part of the holding container 28 is closed by the upper lid 22.

In the preparation step, one end of the tube 23 is connected to the connection port 24 provided in the upper lid 22, and one end of the tube 25 is connected to the connection port 26. One end of a tube 30 is connected to a connection port 29 provided in the holding container 28.

The tube 25 includes a suction device (pump) 32 for sucking air in the container 20 through the tube 25. The tube 30 includes a suction device (pump) 33 which sucks air in the space between the holding container 28 and the container body 21 through the tube 30. As the suction devices (pumps) 32 and 33, for example, a suction source provided in a ward can be used. As the suction devices (pumps) 32 and 33, pumps 32 and 33 which can generate a negative pressure such as a roller pump (tube pump) can also be used. One of the suction devices (pumps) 32 and 33 may be omitted to cause the other suction device to perform the suction of air through the tube 25 and the suction of air through the tube 30.

In the preparation step, the container body 21 in the contracted state as shown in FIG. 1 is brought into an extended state as shown in FIG. 2. Specifically, in the preparation step shown in FIG. 1, the other end of the tube 23 is open, whereby air outside the container body 21 can flow into the container body 21 through the tube 23.

In this state, when the operation of the pump 33 is started, the air in the space between the holding container 28 and the container body 21 is sucked out of the holding container 28 through the tube 30. Meanwhile, outside air can freely flow into the container body 21 through the tube 23. Therefore, the pressure of the space between the holding container 28 and the container body 21 is smaller than the pressure in the container 20 (in the container body 21). Due to such a pressure difference, the container body 21 which has contracted as shown in FIG. 1 is extended in the holding container 28 as shown in FIG. 2. Then, the operation of the suction device (pump) 33 is stopped. When the suction device (pump) 33 is the roller pump, the flow path of the tube 30 is closed by the pump in a state where the operation of the pump is stopped. Through the above preparation step, the container 20 holding the waste liquid treatment composition unit 40 can be set at a position for performing the contact step.

(Contact Step)

Next, the contact step will be described. The contact step is performed in order to bring the waste liquid treatment composition unit 40 into contact with the waste liquid in the container 20 to dissolve the water-soluble member 43 in the waste liquid, thereby causing the waste liquid to contain the flocculant 41 and the boron-containing compound 44.

First, the waste liquid is caused to flow into the container 20. At this time, the waste liquid containing the body fluid is sucked from the other end side of the tube 23. A water stop filter 34 is provided between the connection port 26 of the upper lid 22 and the tube 25. The water stop filter 34 is provided to prevent a part of the waste liquid housed in the container 20 from flowing out of the container 20 and flowing into the tube 25. The water stop filter 34 is configured to stop suction when a part of the waste liquid in the container 20 reaches the water stop filter 34 through the connection port 26.

Specifically, for example, the water stop filter 34 includes a hollow flow path member and an absorber. The flow path member includes a flow path which causes the connection port 26 and the tube 25 to communicate with each other. The absorber is provided in the flow path. The absorber is made of fibers having very excellent liquid absorbability (superabsorbent processed fibers). The absorber has a gap through which air flows, but it instantly swells when absorbing liquid. Accordingly, the water stop filter 34 can stop suction after swelling, which makes it possible to prevent the waste liquid in the container 20 from flowing into the tube 25 in the contact step.

When the operation of the suction device (pump) 32 is started, the waste liquid containing the body fluid is sucked through the tube 23 by the negative pressure generated by discharging the air in the container 20 to the outside of the container body 21 through the tube 25, and flows into the container 20. At this time, in order to maintain the extended state of the container body 21, it is preferable to also operate the suction device (pump) 33.

After the completion of the suction of the waste liquid into the container 20, the tube (piping tube) 25 is removed from the container 20 (specifically, the water stop filter 34). The water stop filter 34 remains attached to connection port 26.

Figure 3:
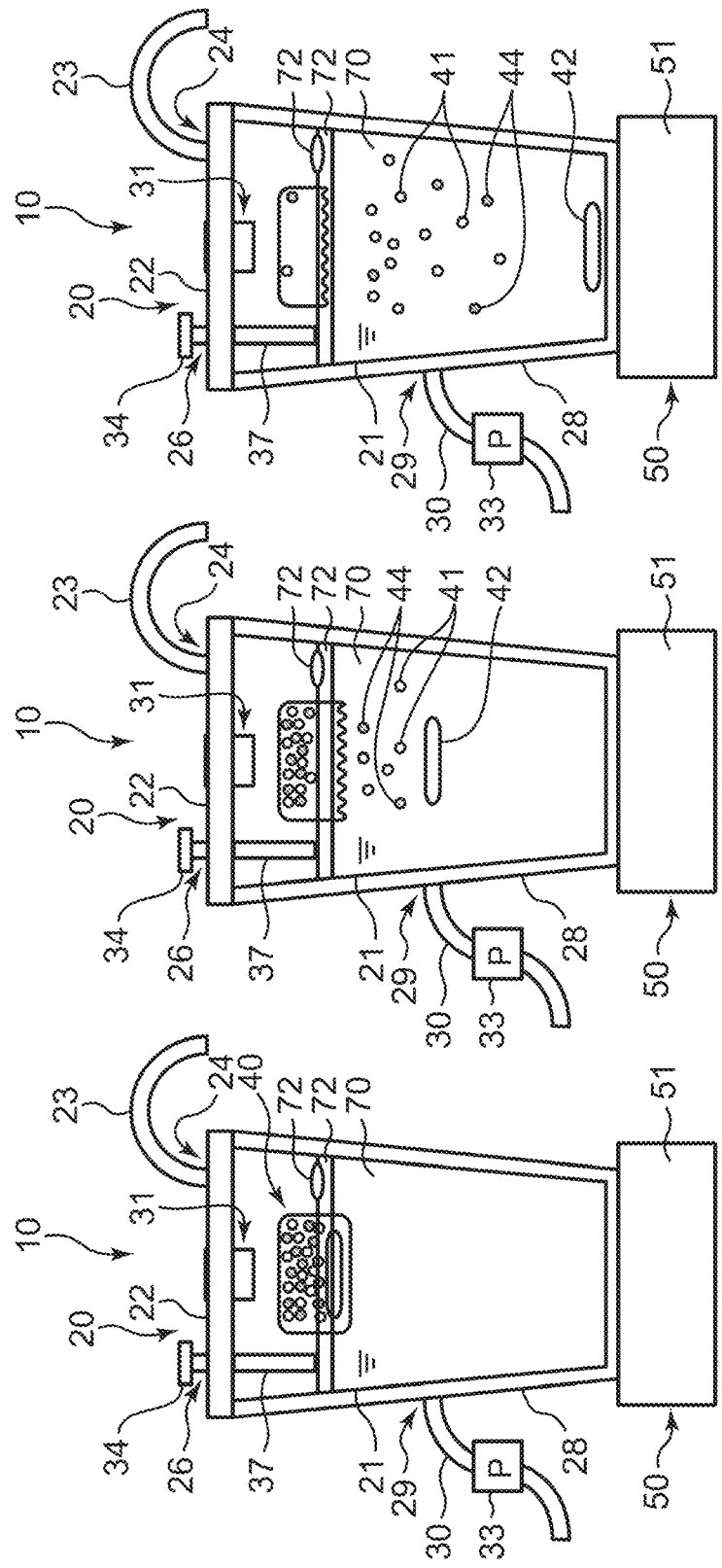
FIG. 3A, FIG. 3B and FIG. 3C are front views showing a process in which a water-soluble member of a waste liquid treatment composition unit dropped into a container is dissolved in a contact step in the present embodiment, so that a stirrer is released from the water-soluble member and falls into a waste liquid, and a process in which a waste liquid treatment composition is released from the water-soluble member and discharged into the waste liquid.

Next, the waste liquid treatment composition unit 40 is dropped into the waste liquid in the container 20. FIG. 3A, FIG. 3B and FIG. 3C are front views schematically showing a drop step. FIG. 3A, FIG. 3B and FIG. 3C are front views showing a process in which the water-soluble member 43 of the waste liquid treatment composition unit 40 dropped into the container 20 is dissolved to release the stirrer 42, and a process in which the flocculant 41 and the boron-containing compound 44 are released into the waste liquid in the drop step.

In the drop step, the dropping button which is an example of the dropping mechanism 31 is pushed down manually by the operator or automatically by the control part of the waste liquid treatment device 10. Accordingly, the waste liquid treatment composition unit 40 supported by the upper lid 22 is detached from the upper lid 22, and falls toward the liquid level of a waste liquid 70.

In the present embodiment, the flocculant 41 and the boron-containing compound 44 are housed in the water-soluble member 43, which makes it possible to prevent the flocculant 41 and the boron-containing compound 44 from being brought into direct contact with the floating substances 72 floating in the waste liquid 70 in a surface layer portion of the waste liquid 70 in the container 20 in this housed state.

In the present embodiment, as described above, the waste liquid treatment composition unit 40 includes the stirrer 42 as the weight adjusting member. Therefore, as shown in FIG. 3A, at least a part of the waste liquid treatment composition unit 40 reaches the waste liquid 70 below the floating substances 72. When the water-soluble member 43 is brought into contact with the waste liquid 70 in this manner, as shown in FIG. 3B, a portion of the water-soluble member 43 which is brought into contact with the waste liquid 70 is gradually dissolved. When a part of the water-soluble member 43 is dissolved, the flocculant 41, the boron-containing compound 44, and the stirrer 42 housed in the housing space of the water-soluble member 43 are exposed to the waste liquid 70. When the dissolution of the water-soluble member 43 further proceeds, the water-soluble member 43 cannot hold the flocculant 41, the boron-containing compound 44, and the stirrer 42, so that a part or all of the flocculant 41 and the boron-containing compound 44, and the stirrer 42 are discharged into the waste liquid 70. As shown in FIG. 3C, most of the flocculant 41 and the boron-containing compound 44 are discharged into the waste liquid 70, and the stirrer 42 drops onto the bottom surface of the container body 21.

In the contact step, it is not necessary to completely dissolve the entire water-soluble member 43, and a part of the water-soluble member 43 may remain without being dissolved.

(Separation Step)

Next, the separation step will be described. The separation step is performed in order to stir the waste liquid 70 containing the flocculant 41 and the boron-containing compound 44 and to separate the waste liquid 70 into the supernatant and the aggregate in the container 20. The separation step includes a stirring step and a leaving step performed after the stirring step.

In the stirring step, the stirrer 42 dropped onto the bottom surface of the container body 21 in the contact step is rotated in the waste liquid 70. The rotation speed or the like of the stirrer 42 is controlled by the main body 51 of the magnetic stirrer 50. In the contact step described above, the waste liquid 70 contains the flocculant 41 and the boron-containing compound 44, and by stirring the waste liquid 70 in the stirring step, the flocculant 41 and the boron-containing compound 44 can be spread throughout the waste liquid 70. As a result, the flocculant 41 and the boron-containing compound 44 efficiently cause the components contained in the waste liquid 70 to become the aggregate.

When the stirring necessary for producing the aggregate is completed, the operation of the magnetic stirrer 50 is stopped. When the container body 21 and the waste liquid 70 in the container body 21 are left to stand, the aggregate precipitates in the container 20, whereby the waste liquid 70 can be separated into the supernatant and the aggregate.

(Discharge Step)

Next, the discharge step will be described. The discharge step is performed to discharge the supernatant from the container 20. Accordingly, the volume of the waste in the container 20 can be reduced. In this discharge step, the supernatant in the container 20 is discharged from the container 20. In the discharge step in the present embodiment, the container body 21 of the container 20 is contracted to reduce the volume of the container body 21, whereby only the supernatant is discharged from the upper part of the container 20 to the outside of the container 20.

At this time, the air and the supernatant in the container 20 are sucked using a suction device (not shown), and discharged to the outside of the container 20. For example, a discharge tube is connected to the connection port 24 of the upper lid 22. The discharge tube includes, for example, a roller pump as the suction device. The discharge step is performed in a state where another opening part such as the connection port 24 is closed.

When the operation of the roller pump is started, the air and the supernatant in the container 20 are sucked, and discharged to the outside of the container 20. By the negative pressure caused by the discharge, the container body 21 is contracted. Accordingly, an aggregate and a small amount of supernatant remain in the container 20 after the container body 21 is contracted.

Only the supernatant may be discharged to the outside of the container 20 from the upper part of the container 20 by applying a pressure to the container body 21 from the outside of the container body 21 to crush the container body 21.

(Discard Step)

Next, the discard step will be described. In the discard step, the container 20 is removed from the holding container 28. The aggregate remaining in the container 20 is subjected to an appropriate treatment such as an incineration treatment together with the container 20, thereby being safely discarded. Furthermore, the aggregate in the supernatant discharged from the container 20 is filtered and separated through a filter (not shown), and then subjected to an appropriate treatment, thereby being safely discarded.

The filter used in the discard step is preferably a large net having an opening size of about (10 mm×10 mm) to (15 mm×15 mm).

In the waste liquid treatment method of the present embodiment, an aggregate which is relatively large and has high strength of aggregation can be obtained, whereby sufficient filtration can be provided even when a filter including a large net as described above is used, and a filtration time is also shortened.

As the filter used in the discard step, a filter having a double structure and formed of the large net and a net having a smaller wire diameter and opening than those of the large net (a medium net or a small net described in Examples to be described later) can also be used. The opening size of the medium net is preferably about (1 mm×1 mm) to (10 mm×10 mm), and the opening size of the small net is preferably (1 mm×1 mm) or less. When the opening size of the filter to be used is too small, clogging occurs also in the waste liquid treatment method of the present embodiment. Therefore, the opening size of each net is preferably greater than at least (50 μm×50 μm) to (100 μm×100 μm).

In the waste liquid treatment method of the present embodiment, the filter used in the discard step has the double structure as described above, and after the supernatant in the container is filtered by the upstream large net, the aggregate which has passed through the large net is captured by the net having a smaller wire diameter and opening than those of the large net, whereby the discharged supernatant is brought into a cleaner state.

As described above, the flocculant 41 and the boron-containing compound 44 are housed in the water-soluble member 43, which makes it possible to prevent the flocculant 41 and the boron-containing compound 44 from being brought into direct contact with the floating substances 72 floating in the waste liquid 70 in the container 20. The waste liquid treatment composition unit 40 is brought into contact with the waste liquid 70 to dissolve the water-soluble member 43 in the waste liquid 70, whereby the flocculant 41 and the boron-containing compound 44 can be released from the dissolved portion to the waste liquid 70 to be brought into contact with the waste liquid 70.

Therefore, it is possible to prevent the following problem from occurring: the flocculant 41 and the boron-containing compound 44 do not sufficiently spread in the waste liquid 70 due to the adhesion of the flocculant 41 and the boron-containing compound 44 to the floating substances 72 before contact with the waste liquid 70. Accordingly, in the contact step, the flocculant 41 and the boron-containing compound 44 can be sufficiently contained in the waste liquid 70, whereby a desired amount of the flocculant 41 and the boron-containing compound 44 can be dispersed in the waste liquid 70 by stirring the waste liquid 70 in the separation step. As a result, the flocculant 41 and the boron-containing compound 44 cause the components contained in the waste liquid 70 to become an aggregate which is relatively large and has high strength of aggregation, whereby the waste liquid 70 can be efficiently separated into the supernatant and the aggregate in the container 20. Since the mixing of the aggregate into the separated supernatant is reduced as much as possible, the formation of an aggregate which is fine and has low strength of aggregation is suppressed, whereby the occurrence of the clogging of the filter can be reduced.

As described above, the present specification discloses techniques of various aspects, among which main techniques are summarized below.

That is, a waste liquid treatment composition according to an aspect of the present invention is a waste liquid treatment composition for treating a waste liquid containing a body fluid to separate the waste liquid into a supernatant and an aggregate in a container, the waste liquid treatment composition comprising: a solid flocculant having at least one group selected from the group consisting of an OH group, an NH group, and an FH group; and a solid compound having at least one group selected from the group consisting of an OH group, an NH group, and an FH group.

The solid flocculant used in the waste liquid treatment composition is preferably at least one selected from the group consisting of a cationic polymer flocculant and an amphoteric polymer flocculant. Preferable examples of the solid compound comprise a boron-containing compound. More specifically, preferable examples thereof include at least one selected from the group consisting of boric acid, ulexite, borax, and kernite. In a preferable embodiment, the waste liquid treatment composition further comprises an oleosity adsorbing agent.

Meanwhile, a waste liquid treatment method according to a further aspect of the present invention comprises: a separation step of housing a waste liquid containing a body fluid in a container, and charging the waste liquid treatment composition of the present embodiment into the waste liquid in the container, followed by stirring to separate the waste liquid into a supernatant and an aggregate; and a step of discarding the supernatant through a filter.

In the waste liquid treatment method, an amount of the solid flocculant charged into the waste liquid is preferably 0.02% by mass or more with respect to the entire waste liquid. An amount of the solid compound charged into the waste liquid is preferably 0.02% by mass or more with respect to the entire waste liquid.

More preferable examples of the waste liquid treatment method include the waste liquid treatment method further comprising a contact step of bringing a waste liquid treatment composition unit containing the waste liquid treatment composition and a water-soluble member into contact with the waste liquid in the container to dissolve a part or a whole of the water-soluble member in the waste liquid, and thus causing the waste liquid to contain the waste liquid treatment composition.

In the waste liquid treatment method, the water-soluble member constituting the waste liquid treatment composition unit is preferably water-soluble paper.

By adopting these configurations, even when the stirring time is not strictly set, the waste liquid can be efficiently processed to obtain an aggregate which is relatively large and has high strength of aggregation, whereby the occurrence of the clogging of the filter can be reduced.

In the waste liquid treatment method, the filter preferably includes a net having an opening of (15 mm×15 mm) or less. In the waste liquid treatment method of the present embodiment, an aggregate which is relatively large and has high strength of aggregation is obtained, whereby sufficient filtration can be provided even when a filter including a large net having an opening as described above is used, and a filtration time is also shortened.

In a preferable embodiment, the filter has a double structure, and includes a first net having an opening of (15 mm×15 mm) or less and a second net having a smaller opening size than that of the first net. In the waste liquid treatment method described above, the filter used in the discard step has the double structure as described above, and after the supernatant in the container is filtered by the upstream first net, the aggregate which has passed through the first net is captured by the second net having a smaller opening size than that of the first net, whereby the discharged supernatant is brought into a cleaner state.

Hereinafter, the present invention will be described in more detail based on Examples, but the following Examples do not limit the present invention at all.

Example 1

Figure 4:
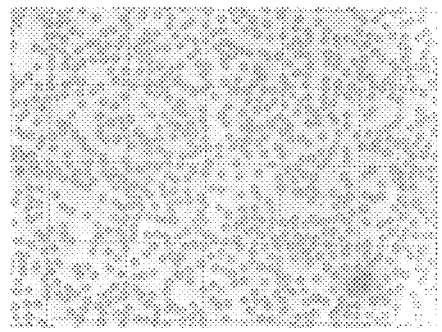
FIG. 4 is a drawing-substituting photomicrograph showing a state where a solution containing 2% of blood is observed with an optical microscope in Example 1.

A solution (4 L) containing 2% (mass ratio; the same applies hereinafter for blood concentration) of blood, which was assumed to be a low concentration blood waste liquid, was used as a sample. To this solution, activated carbon, borax, and a polymer flocculant were added in the following amounts (ratios with respect to the solution), followed by stirring. The number of blood cells before a treatment with a waste liquid treatment composition in the solution containing 2% of blood (hereinafter, for convenience, a treatment until formation of an aggregate in the solution may be referred to as "waste liquid treatment") is 7.5 million/mL as measured with a hemocytometer. FIG. 4 (drawing-substituting photomicrograph) shows a state where the solution containing 2% of blood is observed at a magnification of 100 times with an optical microscope.

(Amount of Each Component Added: Ratio with Respect to Solution)
  Activated carbon: 0.075% by mass
  Borax: 0.062% by mass
  Polymer flocculant (polyacrylic acid ester): 0.075% by mass The aggregates formed in the solution were filtered and separated using two types of nets (large net and medium net) having different opening sizes, which were assumed to be a filter. At this time, the aggregates were allowed to stand for 1 minute after being filtered and separated, and the mass of the aggregate captured on each net, the mass of the aggregate which passed through each net and was captured by a net (hereinafter, referred to as "small net") having a finer opening size (500 μm×500 μm; wire diameter: 0.1 mm), and the ratios of the aggregates were measured. The stirring time was set to two of 4 minutes and 10 minutes. The stirring time of 4 minutes was considered to be most appropriate for the size and strength of aggregation of the aggregate with respect to the solution containing 2% of blood. The stirring time of 10 minutes was sufficient for the waste liquid treatment of a high concentration blood waste liquid and possibly caused once formed flocs to be broken in the waste liquid treatment of a low concentration blood waste liquid.

(Used Net)
  (a) Large net (made of synthetic resin)
    Opening size: 5 mm×5 mm (square)
    Wire diameter: 2.45 to 2.60 mm
  (b) Medium net (made of synthetic resin)
    Opening size: 1.5 mm×1.5 mm (square)
    Wire diameter: 1.96 to 2.0 mm The results are shown in Table 1 below.

TABLE 1

|  | Stirring for 4 minutes | | Stirring for 10 minutes | |
| --- | --- | --- | --- | --- |
|  | Large net | Medium net | Large net | Medium net |
| [Capture fraction] | | | | |
| (g) | 58.6 | 80.0 | 47.1 | 70.0 |
| (% by mass) | 98.0 | 96.2 | 66.6 | 93.0 |
| [Passage fraction] | | | | |
| (g) | 1.27 | 3.13 | 23.60 | 5.35 |
| (% by mass) | 2.12 | 3.77 | 33.40 | 7.10 |

Figure 5A:
FIG. 5A, FIG. 5B and FIG. 5C are drawing-substituting photographs showing states where a sample is subjected to a waste liquid treatment with a stirring time of 4 minutes, and then filtered and separated using a large net in Example 1.
Figure 5B:
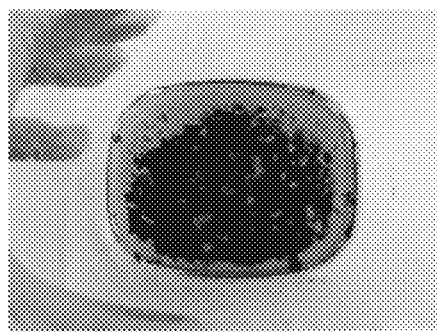
Figure 5C:
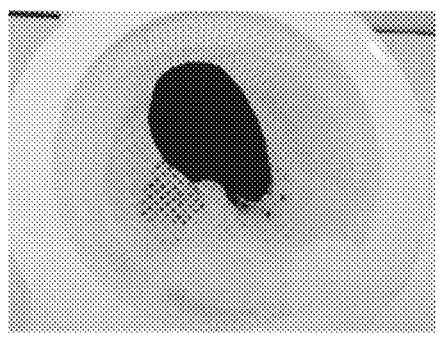

FIG. 5A, FIG. 5B and FIG. 5C (drawing-substituting photographs) show states where the sample is subjected to a treatment with a stirring time of 4 minutes, and then filtered and separated using the large net. FIG. 5A shows the state of the aggregate remaining on the large net; FIG. 5B shows the state of the solution filtered and separated by the large net (corresponding to the supernatant); and FIG. 5C shows the state of the aggregate remaining on the small net.

Figure 6A:
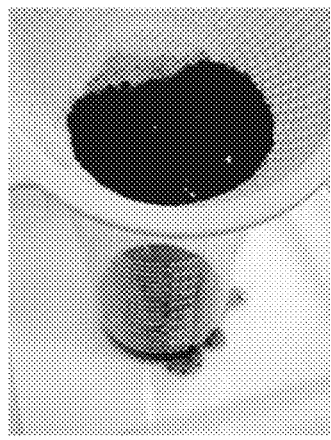
FIG. 6A, FIG. 6B and FIG. 6C are drawing-substituting photographs showing states where a sample is subjected to a waste liquid treatment with a stirring time of 4 minutes, and then filtered and separated using a medium net in Example 1.
Figure 6B:
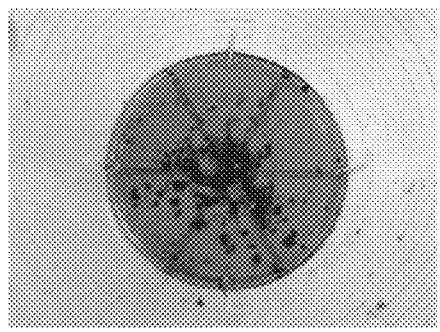
Figure 6C:
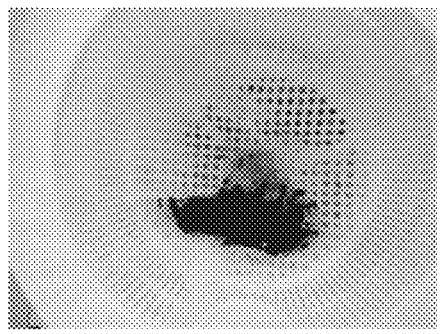

FIG. 6A, FIG. 6B and FIG. 6C (drawing-substituting photographs) shows states where the sample is subjected to a waste liquid treatment with a stirring time of 4 minutes, and then filtered and separated using the medium net. FIG. 6A shows the state of the aggregate remaining on the medium net; FIG. 6B shows the state of the solution filtered and separated by the medium net (corresponding to the supernatant); and FIG. 6C shows the state of the aggregate remaining on the small net.

Figure 7A:
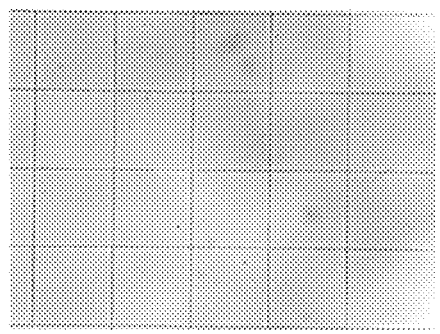
FIG. 7A and FIG. 7B are drawing-substituting photomicrographs showing states where a solution which passes through each net, and then passes through a small net is observed with an optical microscope in Example 1.
Figure 7B:
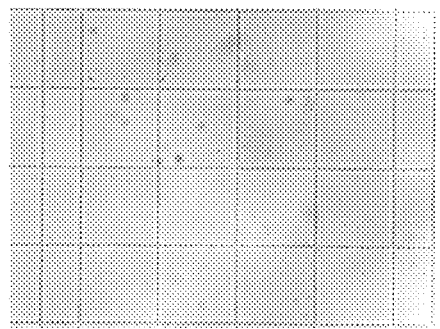

FIG. 7A and FIG. 7B (drawing-substituting photomicrographs) show states where the solution which passes through each net, and then passes through the small net is observed at a magnification of 100 times with an optical microscope.

Figure 8A:
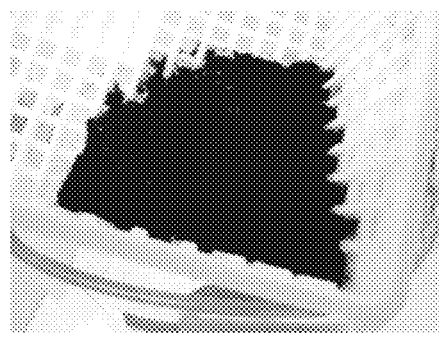
FIG. 8A, FIG. 8B and FIG. 8C are drawing-substituting photographs showing states where a sample is subjected to a waste liquid treatment with a stirring time of 10 minutes, and then filtered and separated using a large net in Example 1.
Figure 8B:
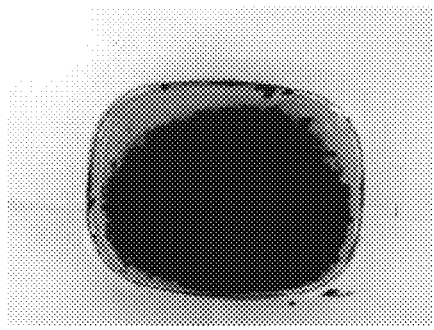
Figure 8C:
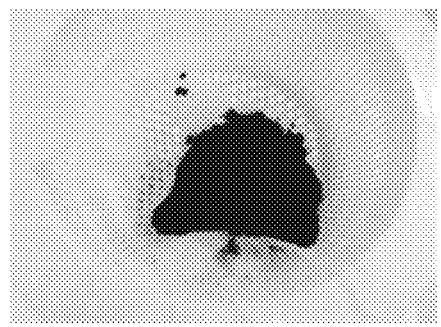

FIG. 7A shows the solution which passes through the large net, and then passes through the small net; and FIG. 7B shows the solution which passes through the medium net, and then passes through the small net. The number of blood cells in the solution shown in FIG. 7A is 620/mL, and the number of blood cellss in the solution shown in FIG. 7B is 3100/mL FIG. 8A, FIG. 8B and FIG. 8C (drawing-substituting photographs) show states where the sample is subjected to a waste liquid treatment with a stirring time of 10 minutes, and then filtered and separated using the large net. FIG. 8A shows the state of the aggregate remaining on the large net; FIG. 8B shows the state of the solution filtered and separated by the large net (corresponding to the supernatant); and FIG. 8C shows the state of the aggregate remaining on the small net.

Figure 9A:
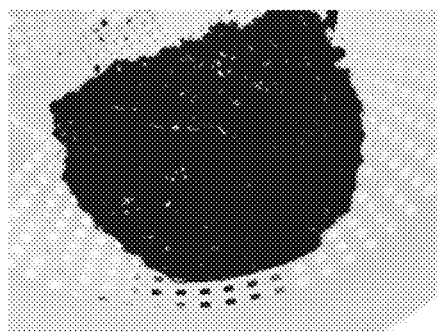
FIG. 9A, FIG. 9B and FIG. 9C are drawing-substituting photographs showing states where a sample is subjected to a waste liquid treatment with a stirring time of 10 minutes, and then filtered and separated using a medium net in Example 1.
Figure 9B:
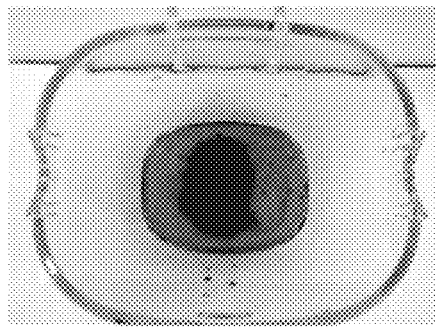
Figure 9C:
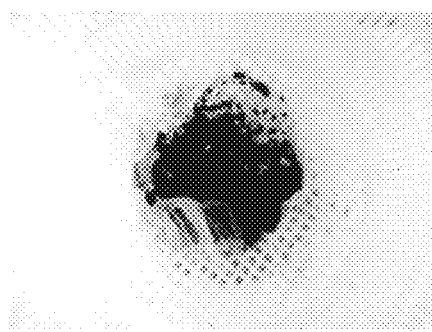

FIG. 9A, FIG. 9B and FIG. 9C (drawing-substituting photographs) show states where the sample is subjected to a waste liquid treatment with a stirring time of 10 minutes, and then filtered and separated using the medium net. FIG. 9A shows the state of the aggregate remaining on the medium net; FIG. 9B shows the state of the solution filtered and separated by the medium net (corresponding to the supernatant); and FIG. 9C shows the state of the aggregate remaining on the small-filter net.

Figure 10:
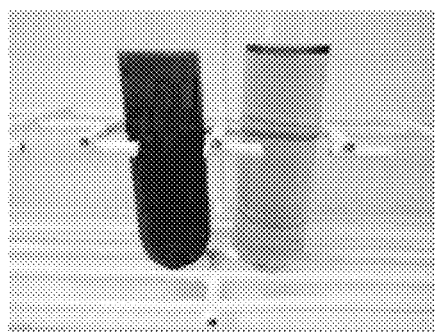
FIG. 10 is a drawing-substituting photograph showing the state of a supernatant after being filtered and separated using a small net in Example 1 in comparison with the state of a solution before treatment.

FIG. 10 (drawing-substituting photograph) shows a state of the supernatant after being filtered and separated using the small net after passing through the medium net in comparison with the state of the solution before the waste liquid treatment. FIG. 10 shows the state of the solution before the waste liquid treatment on the left side and the state of the supernatant after being filtered and separated by the small net on the right side.

A normal waste liquid contains about 10% of blood at maximum, but the stirring time of 10 minutes is a sufficient time for the waste liquid treatment of such a high concentration blood waste liquid (see Example 2 to be described later). The above results indicate that the aggregate is not disintegrated even when the low concentration blood waste liquid is stirred for the stirring time of 10 minutes.

Example 2

A solution (4 L) containing 10% of blood, which was assumed to as a high concentration blood waste liquid, was used as a sample. To this solution, activated carbon, borax, and a polymer flocculant were charged under the same conditions as those in Example 1, followed by stirring for 4 minutes.

The aggregate formed in the solution was sequentially filtered and separated by the large net and the small net used in Example 1. The aggregate formed in the solution was sequentially filtered and separated by the medium net and the small net used in Example 1. At this time, the aggregate was filtered and separated after being stirred for 4 minutes and then left to stand for 3 minutes. The state of the aggregate captured on each net and the state of the supernatant after being filtered and separated by each net were observed.

Figure 11A:
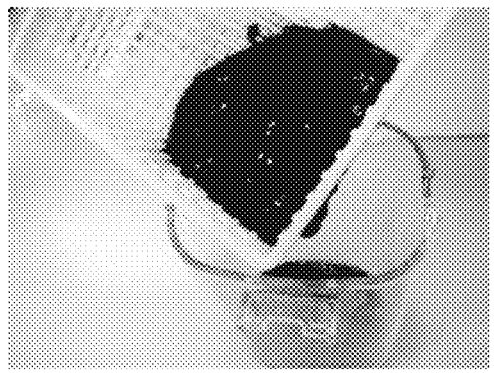
FIG. 11A, FIG. 11B and FIG. 11C are drawing-substituting photographs showing states where a sample is subjected to a waste liquid treatment with a stirring time of 4 minutes, and then filtered and separated using a large net and a small net in Example 2.
Figure 11B:
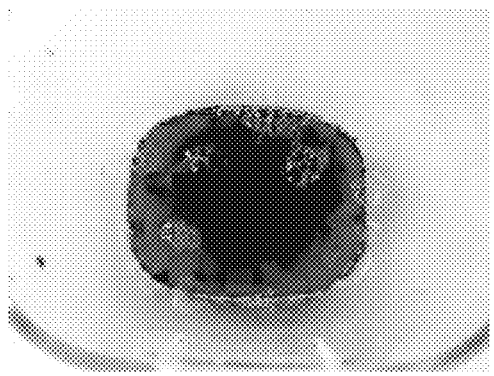
Figure 11C:
Figure 12:
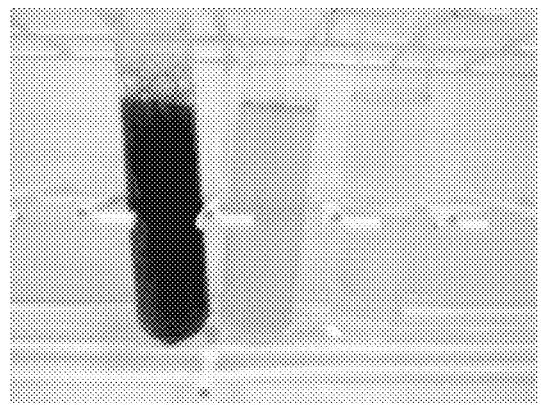
FIG. 12 is a drawing-substituting photograph showing the state of a supernatant after a sample is subjected to a waste liquid treatment with a stirring time of 4 minutes, and then filtered and separated using a medium net or a small net in Example 2 in comparison with the state of a solution before treatment.

FIG. 11A, FIG. 11B and FIG. 11C (drawing-substituting photographs) show states where a solution containing 10% of blood is used as a sample, subjected to a waste liquid treatment, and then filtered and separated using the large net and the small net. FIG. 11A shows the state of the aggregate remaining on the large net; FIG. 11B shows the state of the solution filtered and separated by the large net (corresponding to the supernatant); and FIG. 11C shows the state of the aggregate remaining on the small net. FIG. 12 shows the state of the supernatant after being filtered and separated using the large net or the small net in comparison with the state of a solution before treatment. FIG. 12 shows the state of the solution before the waste liquid treatment on the left side, the state of the supernatant after being filtered and separated using the large net at the center, and the state of the supernatant after being filtered and separated using the small net on the right side.

Figure 13A:
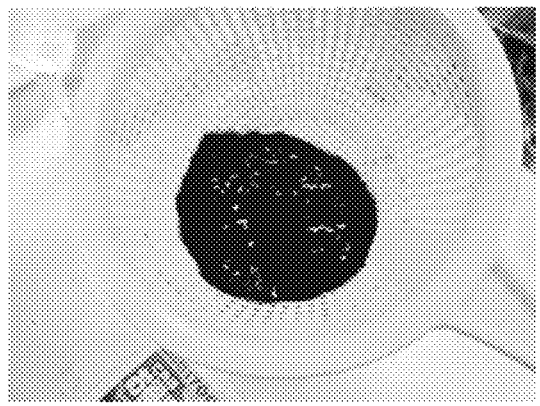
FIG. 13A, FIG. 13B and FIG. 13C are drawing-substituting photographs showing states where a sample is subjected to a waste liquid treatment with a stirring time of 4 minutes, and then filtered and separated using a medium net and a small net in Example 2.
Figure 13B:
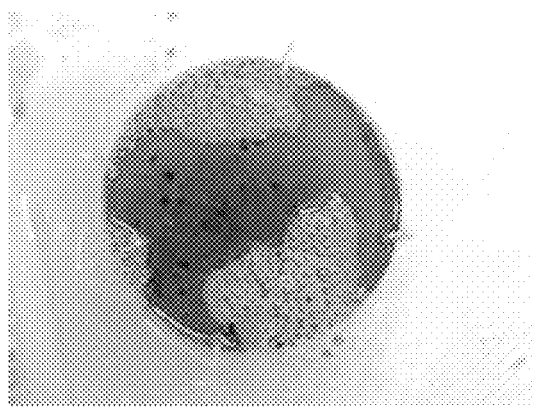
Figure 13C:
Figure 14:
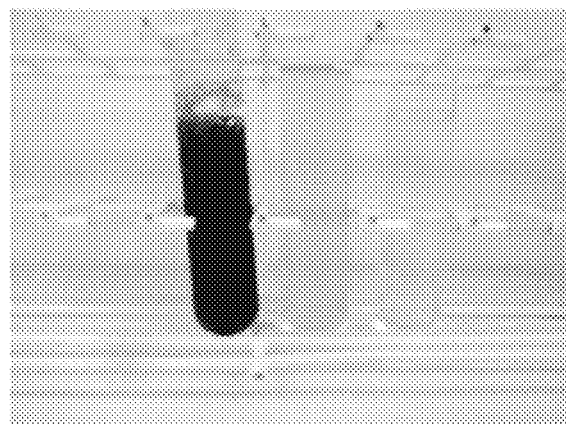
FIG. 14 is a drawing-substituting photograph showing the state of a supernatant after being filtered and separated using a large net or a small net in Example 2 in comparison with the state of a solution before treatment.

FIG. 13A, FIG. 13B and FIG. 13C (drawing-substituting photographs) show states where a solution containing 10% of blood is used as a sample, subjected to a waste liquid treatment, and then filtered and separated using the medium net and the small net. FIG. 13A shows the state of the aggregate remaining on the medium net; FIG. 13B shows the state of the solution filtered and separated by the medium net (corresponding to the supernatant); and FIG. 13C shows the state of the aggregate remaining on the small net. FIG. 14 shows the state of the supernatant after being filtered and separated using the medium net or the small net in comparison with the state of a solution before treatment (the state of the solution containing 10% of blood). FIG. 14 shows the state of the solution before the waste liquid treatment on the left side, the state of the supernatant after being filtered and separated using the medium net at the center, and the state of the supernatant after being filtered and separated using the small net on the right side.

It is found that when the high concentration blood waste liquid as shown in Example 2 is subjected to a waste liquid treatment using the waste liquid treatment composition of the present embodiment, the formation of the aggregate is completed by setting the stirring time to about 4 minutes. The above results indicate that the treatment using a filter having a double structure is useful.

As is apparent from the results of Examples 1 and 2, it can be seen that when the waste liquid treatment is performed using the waste liquid treatment composition containing activated carbon, borax, and a polymer flocculant, the waste liquid can be effectively treated with generating an aggregate which is relatively large and has sufficient strength of aggregation, and without generating an aggregate which causes the clogging of the filter, even if the stirring time is not strictly set according to the blood concentration in the waste liquid (for example, by setting the stirring time to about 4 minutes).

Comparative Example

A solution (4 L) containing 2% of blood, which was used in Example 1 was used as a sample. To this solution, activated carbon and a polymer flocculant were added in the following amounts, followed by stirring for 10 minutes. At this time, a similar experiment was performed using a solution (4 L) containing 10% of blood cells, which was assumed to be a high concentration blood waste liquid, as a sample. The number of blood before a waste liquid treatment in the solution containing 10% of blood is 39.5 million/mL as measured with a hemocytometer.

(Amount of Each Component Added: Ratio with Respect to Waste Liquid)
   Activated carbon: 0.075% by mass
   Polymer flocculant (polyacrylic acid ester): 0.075% by mass The aggregate formed in the waste liquid was filtered and separated in the same manner as in Example 1 using two types of nets shown in Example 1.

Figure 15A:
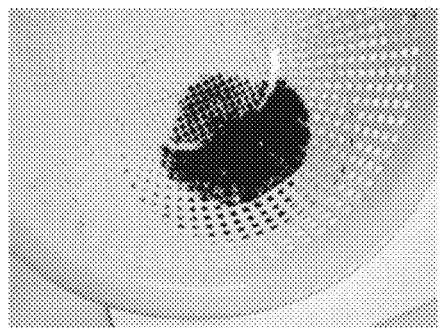
FIG. 15A and FIG. 15B are drawing-substituting photographs showing states where a solution containing 2% of blood is used as a sample, subjected to a waste liquid treatment, and then filtered and separated using a medium net in Comparative Example.
Figure 15B:
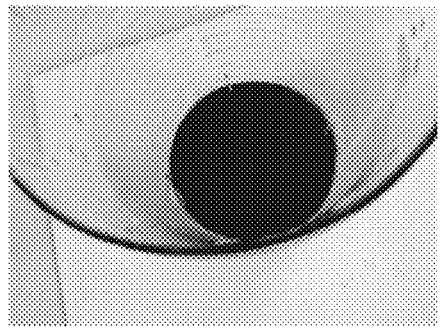
Figure 16:
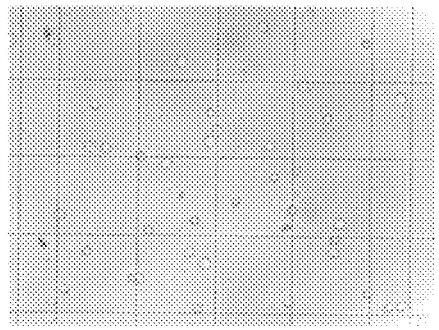
FIG. 16 is a drawing-substituting photomicrograph showing a state where the solution shown in FIG. 15B is observed with an optical microscope in Comparative Example.

FIG. 15A and FIG. 15B (drawing-substituting photographs) show states where the solution containing 2% of blood is used as a sample, subjected to the waste liquid treatment, and then filtered and separated using a medium net. FIG. 15A shows the state of the aggregate remaining on the medium net, and FIG. 15B shows the state of the solution (corresponding to the supernatant) filtered and separated by the medium net. FIG. 16 (drawing-substituting photomicrograph) shows a state where the solution shown in FIG. 15B is observed at a magnification of 100 times with an optical microscope.

Figure 17A:
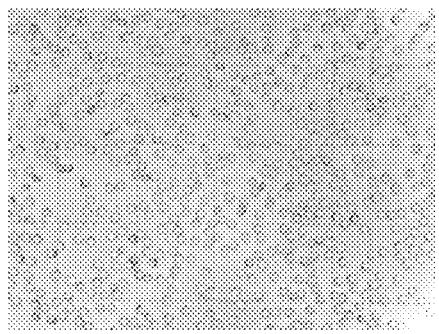
FIG. 17A and FIG. 17B are drawing-substituting photomicrographs showing states where a solution containing 10% of blood before and after a waste liquid treatment in Comparative Example is observed with an optical microscope.
Figure 17B:
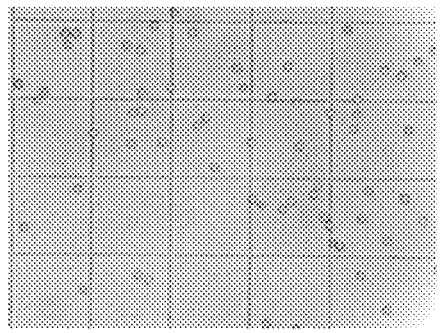

FIG. 17A and FIG. 17B (drawing-substituting photomicrographs) show the states of the solution (4 L) containing 10% of blood before and after the waste liquid treatment. FIG. 17A shows the state of the solution containing 10% of blood before the waste liquid treatment (for convenience of observation, a solution diluted to 10 times was used), and FIG. 17B shows the state of the solution containing 10% of blood after the waste liquid treatment. The states are observed at a magnification of 100 times with an optical microscope.

Figure 18:
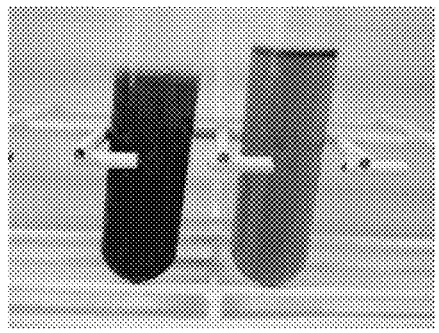
FIG. 18 is a drawing-substituting photograph showing the solution shown in FIG. 15B in comparison with a state before a waste liquid treatment in Comparative Example.

FIG. 18 (drawing-substituting photograph) shows the state of the solution after the waste liquid treatment shown in FIG. 17B in comparison with the state of a solution before treatment (the state of the solution containing 10% of blood). FIG. 18 shows the state of the solution before the waste liquid treatment on the left side, and the state of the solution after the treatment on the right side. The number of blood cells in the solution shown in FIG. 17B is 370,000/mL as measured with a hemocytometer.

As is apparent from these results, it is found that when the waste liquid treatment is performed only with the activated carbon and the polymer flocculant without containing borax, blood in the waste liquid sufficiently remains in the solution without being sufficiently coagulated by the aggregate. Such blood is likely to form an aggregate which is fine and has low strength of aggregation, which causes the clogging of the filter.

Example 3

A solution (5 L) containing 2% of blood, which was assumed to be a low concentration blood waste liquid, was used as a sample. To this solution, activated carbon, borax, and a polymer flocculant were added in the following amounts, followed by stirring for 4 minutes. That is, in Example 3, the amount of borax in the waste liquid treatment composition is increased 10 times as large as that in Example 1.

(Amount of Each Component Added: Ratio with respect to Solution)

Activated carbon: 0.075% by mass
Borax: 0.62% by mass
Polymer flocculant (polyacrylic acid ester): 0.075% by mass The aggregate formed in the waste liquid was filtered and separated using the small net described above. At this time, the aggregate was filtered and separated after being stirred and then left to stand for 1 minute.

Figure 19A:
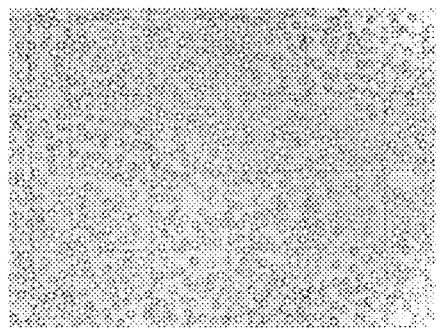
FIG. 19A and FIG. 19B are drawing-substituting photomicrographs showing states where a supernatant after being filtered and separated using a small net is observed with an optical microscope in Example 3 in comparison with a state before a waste liquid treatment.
Figure 19B:
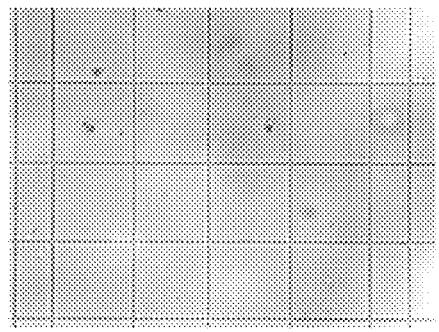

FIG. 19A and FIG. 19B (drawing-substituting photomicrographs) show states where the solution before and after a waste liquid treatment is observed at a magnification of 100 times with an optical microscope. FIG. 19A shows the state of the solution before the waste liquid treatment, and substantially corresponds to the state shown in FIG. 4. FIG. 19B shows the state of the solution after the waste liquid treatment, and blood in the solution is found to be sufficiently removed.

Figure 20:
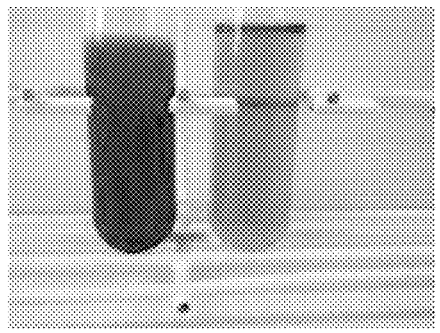
FIG. 20 is a drawing-substituting photograph showing the state of a supernatant after being filtered and separated using a small net in Example 3 in comparison with a state before a waste liquid treatment.

FIG. 20 (drawing-substituting photograph) shows the states of the solution before and after the waste liquid treatment. FIG. 20 shows the state of the solution before the waste liquid treatment on the left side, and the state of the solution after the waste liquid treatment on the right side.

As is apparent from these results, it is found that even when the waste liquid treatment composition in which the content of borax is increased by 10 times is used, the waste liquid can be effectively treated with generating an aggregate which is relatively large and has sufficient strength of aggregation and without generating an aggregate which cause the clogging of the filter.

This application is based on Japanese Patent Application No. 2019-11239 filed on Jan. 25, 2019, the contents of which are included in the present application.

The present invention has been appropriately and sufficiently explained above by way of the embodiments while referring to the specific examples and drawings described above, for the purpose of illustrating the invention. A person skilled in the art should recognize, however, that the embodiments described above can be easily modified and/or improved. Therefore, it is understood that any modified embodiments or improved embodiments conducted by a person skilled in the art are encompassed within the scope as claimed in the appended claims, so long as these modifications and improvements do not depart from the scope of the claims.

INDUSTRIAL APPLICABILITY

A waste liquid treatment composition and a waste liquid treatment method of the present invention are very useful in treatment of a waste liquid containing a body fluid, and the like, and thus have wide industrial applicability in technical fields such as medical care and a waste treatment.

The invention claimed is:

1. A waste liquid treatment method comprising:
a separation step of housing a waste liquid containing blood and a body fluid in a container, and charging a waste liquid treatment composition into the waste liquid in the container, followed by stirring from 4 minutes to 10 minutes to separate the waste liquid into a supernatant and an aggregate; and
a step of discarding the supernatant through a filter, wherein
the waste liquid treatment composition is for treating the waste liquid to separate the waste liquid into the supernatant and the aggregate in the container, and
the waste liquid treatment composition comprises a solid flocculant, which is at least one selected from the group consisting of a cationic polymer flocculant and an amphoteric polymer flocculant, and a solid compound, which is a boron-containing compound.

2. The waste liquid treatment method according to claim 1, wherein an amount of the solid flocculant charged into the waste liquid is 0.02% by mass or more with respect to the entire waste liquid.

3. The waste liquid treatment method according to claim 1, wherein an amount of the solid compound charged into the waste liquid is 0.02% by mass or more with respect to the entire waste liquid.

4. The waste liquid treatment method according to claim 1, further comprising a contact step of bringing a waste liquid treatment composition unit containing the waste liquid treatment composition and a water-soluble member housing the waste liquid treatment composition into contact with the waste liquid in the container, to dissolve a part or a whole of the water-soluble member in the waste liquid, and thus causing the waste liquid to contain the waste liquid treatment composition.

5. The waste liquid treatment method according to claim 4, wherein the water-soluble member constituting the waste liquid treatment composition unit is water-soluble paper.

6. The waste liquid treatment method according to claim 1, wherein the filter includes a net having an opening of (15 mm×15 mm) or less.

7. The waste liquid treatment method according to claim 1, wherein the filter has a double structure, and includes a first net having an opening of (15 mm×15 mm) or less and a second net having a smaller opening size than that of the first net.

8. The waste liquid treatment method according to claim 1, wherein the boron-containing compound is at least one selected from the group consisting of boric acid, ulexite, borax, and kernite.

9. The waste liquid treatment method according to claim 1, wherein the waste liquid treatment composition further comprises an oleosity adsorbing agent.

10. The waste liquid treatment method according to claim 1, wherein the solid flocculant is the cationic polymer flocculant.

11. The waste liquid treatment method according to claim 8, wherein the boron-containing compound is borax.

12. The waste liquid treatment method according to claim 1, wherein the waste liquid contains 2% to 10% of blood.

* * * * *